US010780062B2

(12) United States Patent
Sievers

(10) Patent No.: US 10,780,062 B2
(45) Date of Patent: Sep. 22, 2020

(54) TOBACCO PRODUCTS

(71) Applicant: COLORADO CAN LLC, Boulder, CO (US)

(72) Inventor: Robert E. Sievers, Boulder, CO (US)

(73) Assignee: COLORADO CAN LLC, Boulder, CO (US)

( * ) Notice: Subject to any disclaimer, the term of this patent is extended or adjusted under 35 U.S.C. 154(b) by 0 days.

(21) Appl. No.: 16/361,800

(22) Filed: Mar. 22, 2019

(65) Prior Publication Data

US 2019/0216748 A1    Jul. 18, 2019

Related U.S. Application Data

(60) Continuation of application No. 15/894,087, filed on Feb. 12, 2018, which is a division of application No. 13/642,878, filed as application No. PCT/US2011/033587 on Apr. 22, 2011, now Pat. No. 9,895,321.

(60) Provisional application No. 61/327,323, filed on Apr. 23, 2010, provisional application No. 61/439,799, filed on Feb. 4, 2011.

(51) Int. Cl.
| | |
|---|---|
| *A61K 31/047* | (2006.01) |
| *A61K 9/00* | (2006.01) |
| *A61K 9/16* | (2006.01) |
| *A61K 9/51* | (2006.01) |
| *A61K 39/12* | (2006.01) |
| *A61K 45/06* | (2006.01) |
| *A61K 39/00* | (2006.01) |
| *A61K 39/165* | (2006.01) |

(52) U.S. Cl.
CPC .......... *A61K 31/047* (2013.01); *A61K 9/0056* (2013.01); *A61K 9/0075* (2013.01); *A61K 9/1647* (2013.01); *A61K 9/1688* (2013.01); *A61K 9/1694* (2013.01); *A61K 9/5153* (2013.01); *A61K 9/5192* (2013.01); *A61K 39/12* (2013.01); *A61K 39/165* (2013.01); *A61K 45/06* (2013.01); *A61K 2039/54* (2013.01); *A61K 2039/542* (2013.01); *A61K 2039/543* (2013.01); *A61K 2039/544* (2013.01); *A61K 2039/60* (2013.01); *C12N 2760/18434* (2013.01)

(58) Field of Classification Search
CPC .. A61K 2300/00; A61K 39/12; A61K 31/047; A61K 39/165; A61K 2039/544; A61K 9/0075; A61K 2039/54; A61K 2039/542; A61K 2039/543; A61K 2039/60; A61K 45/06; A61K 9/0056; A61K 9/1647; A61K 9/1688; A61K 9/1694; A61K 9/5153; A61K 9/5192; A61K 2039/6031; A61K 39/00; A61K 47/10; A61K 47/183; A61P 35/00; A61P 31/20; A61P 37/00
See application file for complete search history.

(56) References Cited

U.S. PATENT DOCUMENTS

| | | |
|---|---|---|
| 5,576,014 A | 11/1996 | Mizumoto et al. |
| 6,165,471 A | 12/2000 | Garcea et al. |
| 6,630,121 B1 | 10/2003 | Sievers et al. |
| 7,763,529 B2 | 7/2010 | Garcea et al. |
| 2003/0004142 A1 | 1/2003 | Prior et al. |
| 2004/0141950 A1 | 7/2004 | Noelle et al. |
| 2008/0014260 A1 | 1/2008 | Seager |
| 2008/0035143 A1 | 2/2008 | Sievers et al. |
| 2009/0229535 A1 | 9/2009 | Garcea et al. |
| 2011/0033893 A1 | 2/2011 | Garcea et al. |
| 2014/0088045 A1* | 3/2014 | Rigas ................... A24B 15/16 514/81 |

OTHER PUBLICATIONS

Lam et al, Cancer Epidemiol. Biomarkers Prev., 15:1526-1531 (2006).
Gustafson et al, Science Translational Medicine, 2(26)26ra25:1-11 (2010).
Burger et al, Journal of Aerosol Medicine and Pulmonary Drug Delivery, 21(1):25-34 (2008).
Moody-Haupt et al, Journal of Molecular Biology, 297:409-420 (2000).
Schofield et al, Nature, 418(15):785-789 (2002).
McAdams et al, Poster: Myo-Inositol as a Stabilizing Excipient for Inhaled Dry Aerosol Vaccines and Pharmaceuticals, Presented at RDD Europe, May 19-22, 2009, Lisbon, Portugal.
Cape et al, Poster: Inhalable Dry Powder Live-Attenuated Measles Virus Vaccine Prepared by teh CAN-BD Process, a Novel Spray Drying Alternative to Lyophilization, Presented at 2010 CHI PepTalk, Jan. 11-15, 2010, San Diego, CA.
McAdams et al, Poster: Characterization of Myo-Inositol as a Particle-Forming and Stabilizing Excipient for Inhalable Measles and Human Papillomavirus Vaccines, Presented at 2010 Respiratory Drug Delivery conference, Apr. 25-29, 2010, Orlando, FL.
Clinical Trials, Inositol in Preventing Lung Cancer in Patients With Bronchial Epthelial Dysplasia Who Are Current or Former Smokers, U.S. National Library of Medicine, pp. 1-15 (2010).

* cited by examiner

*Primary Examiner* — Umamaheswari Ramachandran
(74) *Attorney, Agent, or Firm* — Porter Wright Morris & Arthur LLP

(57) ABSTRACT

A tobacco product includes a dry powder composition comprising an amount of myo-inositol effective for treating and/or delaying onset of dysplastic lesions in the bronchial airway of an individual. A method for administering myo-inositol to an individual comprises the individual consuming the tobacco product.

13 Claims, 4 Drawing Sheets

TOBACCO PRODUCTS

RELATED APPLICATIONS

This application is a continuation of U.S. application Ser. No. 15/894,087 filed Feb. 12, 2018, which is a divisional application of U.S. application Ser. No. 13/642,878 filed Apr. 8, 2013, now U.S. Pat. No. 9,895,321, which is a 371 of PCT/US2011/033587 filed Apr. 22, 2011, and claims priority to U.S. Applications Nos. 61/327,323 filed Apr. 23, 2010 and 61/439,799 filed Feb. 4, 2011.

FIELD OF THE INVENTION

The present invention relates to methods and products for treating and/or delaying onset of dysplastic lesions.

BACKGROUND OF THE INVENTION

There are certain highly contagious diseases that, despite the availability of vaccines, continue to be serious health problems in developing and, in some cases, developed countries. For example, measles is a highly contagious human disease caused by the measles virus (MV), and vaccination programs have dramatically reduced its incidence. However, despite the success of global measles vaccination programs, measles was still responsible for an estimated 345,000 deaths in 2005, with most of these deaths occurring in developing countries. Measles outbreaks also continue to occur in developed countries that have failed to maintain a high level of population immunity. Global vaccination coverage is approximately 80% but, according to WHO estimates, more than 23 million infants did not receive their first dose of measles-containing vaccine in 2007. Tuberculosis is also a highly contagious disease that, despite the availability of vaccines, continues to be a serious health problem. Many significant developments have been made in the field of human papillomavirus (HPV) vaccines. See, for example, the Garcea et al U.S. Pat. Nos. 6,165,471, 7,763,259, 2009/0229535 and 2011/0033893. Additionally, HPV vaccines are now commercially available. However, their use in developing countries is hampered by conditions necessary for administration. Safety, disposal, and wastage issues associated with using current lyophilized vaccines that require reconstitution with clean water and use of needles for injection remain a concern and limit widespread coverage in certain countries. New vaccine formulations for diseases such as these that are more easily administered, stable at ambient temperatures, easily transported, and cost effective would be beneficial.

Aerosol delivery of measles vaccines have been employed and overcome at least some of the disadvantages of needle-administered vaccines. Several clinical studies have been performed using aerosol measles vaccination by nebulizing commercial lyophilized formulations after reconstitution, and this route of administration resulted in equal or better immune responses in children greater than 10 months of age compared with injection. Additionally, dry powder vaccine formulations adapted for administration by inhalation are disclosed in the Sievers et al U.S. Patent Application No. 2008/0035143 A1 and employ carriers such a myo-inositol and/or maltodextrin. Such dry powder formulations are advantageous in avoiding needle delivery and the need for reconstituting water, and may be supplied in unit dosage form to avoid waste. However, additional means for facilitating effective vaccination are desired as well.

SUMMARY OF THE INVENTION

The present invention is directed to, inter alia, vaccines, methods of administering vaccines, optionally with adjuvants, methods for providing storage stable unit dosages of vaccine, methods and products for treating and/or delaying onset of dysplastic lesions, wafers for oral administration.

More specifically, in one embodiment, the present invention is directed to methods of treating and/or delaying onset of dysplastic lesions in the bronchial airway of an individual. The methods comprise delivering to the respiratory track of the individual an inhalable dry powder composition including an effective amount of myo-inositol.

In another embodiment, the invention is directed to a tobacco product which includes a dry powder composition comprising an amount of myo-inositol effective for treating and/or delaying onset of dysplastic lesions in the bronchial airway of an individual tobacco smoker.

In another embodiment, the present invention is directed to additional methods of treating and/or delaying onset of dysplastic lesions in the bronchial airway of an individual. These methods comprise sublingually delivering a wafer comprising an effective amount of myo-inositol to the individual.

In yet another embodiment, the present invention is directed to methods for administering a vaccine to an individual. The methods comprise administering a first portion of the vaccine to the individual sublingually and administering a second portion of the vaccine to the individual by an administration route other than sublingually, wherein the first portion and the second portion combined provide an effective amount of the vaccine.

In a further embodiment, the present invention is directed to additional methods for administering a vaccine to an individual. The methods comprise administering a first portion of the vaccine to the individual via a first route comprising sublingually, orally to the gastrointestinal tract, inhalation, or injection, and administering a second portion of the vaccine to the individual by an administration route other than the first route, wherein the first portion and the second portion combined provide an effective amount of the vaccine.

In another embodiment, the present invention is directed to a vaccine in the form of an inhalable dry powder composition comprising a combination of nanoparticles having a diameter less than 1 µm and microparticles having a diameter greater than 2.0 µm, wherein the dry powder composition comprises at least about 10% particles having a diameter not greater than about 3 µm, at least about 10% particles having a diameter of about 5-10 µm, and at least about 10% particles having a diameter of at least about 20 µm.

In another embodiment, the invention is directed to a wafer comprising a compressed dry powder composition comprising myo-inositol, wherein the wafer has a thickness of not greater than about 2 mm and dissolves in water at room temperature in less than one minute. The wafer is suitable for oral administration of therapeutic agents.

In another embodiment, the invention is directed to a wafer comprising a compressed dry powder composition comprising a vaccine and a carrier, wherein the wafer has a thickness of not greater than about 2 mm and dissolves in water at room temperature in less than about one minute.

In another embodiment, the invention is directed to methods of providing storage stable unit dosages of a vaccine. The methods comprise individually packaging unit dosages of a dry powder composition comprising the vaccine and a carrier in blister compartments formed of gas and moisture resistant material.

The various embodiments of the invention provide improved methods and products for administration of therapeutic agents, including, but not limited to vaccines, and may provide advantages of conventional methods and/or products.

BRIEF DESCRIPTION OF THE DRAWINGS

The following detailed description will be more fully understood in view of the Drawings, in which:

FIGS. 5A and 5B show powder mass and measles vaccine virus titer distribution on the short-stack Andersen Cascade Impactor (ACI) Stages 0, 1, 3 and 5, as described in Example 4.

DETAILED DESCRIPTION

Figure 1:
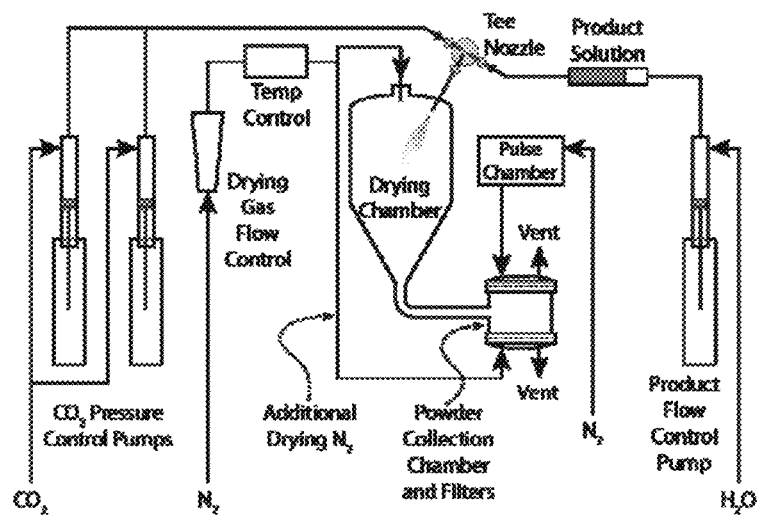
FIG. 1 sets forth a schematic view of a Carbon dioxide-Assisted Nebulization with a Bubble Dryer (CAN-BD) process which may be used to form dry powder compositions for use in the present invention.

The methods and products of the present invention, in certain embodiments, employ dry powder compositions. In one embodiment, the dry powder compositions may be formed by the techniques disclosed in the Sievers et al U.S. Pat. No. 6,630,121, incorporated herein in its entirety by reference, which techniques are employed in the commercially available Carbon dioxide-Assisted Nebulization with a Bubble Dryer (CAN-BD), although the dry powder compositions may be formed by other techniques known in the art, as well. CAN-BD is a closed, continuous process wherein dense carbon dioxide (for example, supercritical or near supercritical carbon dioxide) and a liquid aqueous solution or suspension are intimately mixed in a low volume mixing tee at room temperature and very high pressure (for example about 80 bar), and the resulting emulsion mixture is rapidly expanded through a flow restrictor (for example, having an inside diameter of about 75 to 380 µm) into a drying chamber at or near atmospheric pressure to generate aerosols of microbubbles and microdroplets. Warm nitrogen gas is used to maintain the drying chamber at near ambient temperatures, i.e., below about 60° C., to dry the aerosols and generate dry powders containing less than 5 weight percent water. In many cases, the dry powders contain less than 2%, less than 1% or less than 0.5% by weight water. Typically, the dry powder compositions will include a carrier, for example, myo-inositol, sucrose, lactose, mannitol, sorbitol, trehalose, one or more amino acids, peptides, polylactic-glycolic acid (PLGA), polylactic acid (PLA), lecithin, dispalmitoylphosphatidylcholine (DPPC), maltodextrin, or the like.

In a specific embodiment of the CAN-BD for use in preparing dry powder compositions for various embodiments of the present invention, a water/oil/water (w/o/w) emulsion is mixed with dense carbon dioxide. Water-in-oil-in-water (w/o/w) emulsions are a multiple emulsion system in which the internal and external aqueous phases are separated by an oily lipophilic layer. The w/o/w system consists of internal aqueous drops surrounded by a surfactant film, with an aqueous layer with a surfactant boundary film in turn surrounding these internal drops. Typically, for drug preparations, the drug is dissolved in the inner aqueous phase, poly (lactic-co-glycolic acid) (PLGA) is dissolved in a volatile organic solvent, for example, dichloromethane, ethyl acetate or acetone, forming the oily phase and an emulsifier is dissolved in the outer aqueous phase. Use of the CAN-BD system causes rapid elimination of the volatile organic phase and polymer (PLGA) precipitation and solid drug-loaded microspheres are formed upon drying. In a more specific embodiment, the w/o/w emulsion comprises a drug dissolved or suspended in water/polylactic-glycolic acid in dichloromethane or ethyl acetate as an organic phase/water with stabilizing polyvinyl alcohol.

In certain embodiments of the invention, the dry powder compositions may comprise myo-inositol (cis-1,2,3,5-trans-4,6-cyclohexanehexol). Dry powder compositions comprising myo-inositol are disclosed in the Sievers et al U.S. Patent Application No. 2008/0035143 A1, incorporated herein in its entirety, although other myo-inositol dry powder compositions, including those generally and/or specifically disclosed herein are also suitable for use in embodiments of the present invention. Dry powder compositions comprising myo-inositol may optionally further include one or more of amino acids, for example, arginine, alanine, histidine, leucine, and/or methionine, surfactants, for example, palmitic acid, stearic acid, Tween 20, Tween 80, and/or Pluronic F68, stabilizers, buffers, for example, tricine, sodium or potassium phosphate, sodium acetate, and/or sodium citrate, metal chelating agents, for example EDTA and/or DTPA, gelatin, albumin, or the like. In one specific embodiment, myo-inositol and leucine are employed in a 98.5:1.5 weight ratio. Advantageously, myo-inositol dry powder compositions containing one or more additional components are provided using the CAN-BD process. It has been discovered that when pure myo-inositol is processed by the CAN-BD process at a temperature of about 50° C., a crystal polymorph which is different from the common crystal polymorph of native myo-inositol forms. This polymorph has an exothermic transition with onset of 110-130° C. and appears to be thermally stable at room temperature for only short periods of time (less than 2 weeks), but remains for longer periods of time when stored at temperatures of 2-8° C. (for at least 3 months and up to 5 months), and is removed by annealing at 115° C. or above. The moisture content of this new polymorph is very low (0.1% water) and identical to the moisture content of native myo-inositol. The X-ray diffraction pattern of this polymorph differs from those of native myo-inositol and a previously disclosed myo-inositol dihydrate (Bonnet 2006). Processing pure myo-inositol using the CAN-BD process at temperatures at 60° C. and above provides the common crystal polymorph of native myo-inositol.

In specific embodiments, the dry powder compositions of myo-inositol comprise a fine particle fraction (as measured according to the Andersen Cascade Impactor (ACI) and USP Chapter <601>) of less than about 5.8 µm of at least about 20%, and in a more specific embodiment, a fine particle fraction less than about 3.3 µm of at least about 10%. In further embodiments, the dry powder compositions of myo-inositol comprise a fine particle fraction of less than about 5.8 µm ranging from about 35 to about 50%, and a fine particle fraction less than about 3.3 µm ranging from about 15 to about 30%. In a specific embodiment, these dry powder compositions of myo-inositol further include leucine, for example, in a myo-inositol:leucine weight ratio in a range of from about 90.0:10.0 to about 99.5:0.5.

In a first embodiment, the invention is directed to methods of treating and/or delaying onset of dysplastic lesions in the bronchial airway of an individual. In a specific embodiment, the individual is a tobacco smoker. Within the present disclosure and claims, the term "tobacco smoker" is used to refer to current and former tobacco smokers. Cigarette smoke is a dominant cause of lung cancer, but the damage caused by cigarette smoke is not limited solely to the lung. Rather, cigarette smoke forms a field of injury throughout the entire respiratory tract. Mild to moderate dysplasia in the form of dysplastic lesions in the respiratory tract represent an early abnormal change in the cytology of cells that is non-cancerous but is often considered a precancerous state. Lam et al, *Cancer Epidemiol. Biomarkers Prev.,* 15:1526-1531 (2006) previously studied the use of myo-inositol for lung cancer chemoprevention wherein smokers and former smokers with mild to moderate airway dysplasia were treated with myo-inositol for three months by oral administration of doses up to 30 grams per day to the gastrointestinal tract, with the maximum tolerated dose being 18 grams per day. A significant regression in dysplastic lesions was observed. Gustafson et al, *Science Translational Medicine,* 2(26) 26ra25:1-11 (2010) have determined that airway P13K pathway activation is an early and reversible event in lung cancer development and concluded that myo-inositol is a P13K inhibitor and its lung cancer chemoprevention properties may be related to this inhibition.

The present methods therefore employ myo-inositol in treating and/or delaying onset of dysplastic lesions in the bronchial airway of an individual. In one embodiment, the methods comprising delivering to the respiratory track of the individual an inhalable dry powder composition including an effective amount of myo-inositol. The inhalable powder may, but is not required to, be prepared according to the CAN-BD techniques described above. The effective amount will be dependent on the extent of any existing dysplasia and the condition of the individual to be treated. One of ordinary skill in the art ill appreciate that the targeted therapy of the present methods will advantageously allow the use of effective doses which are generally lower than the systemic administration employed by Lam et al. In one embodiment, the effective amount comprises from about 0.01 to about 10 grams per day, and in more specific embodiments, can be from about 0.5 to about 10, from about 1 to about 10, from about 0.01 to about 5, from about 0.5 to about 5, from about 1 to about 5, grams per day. The dry powder composition may include one or more excipients, for example, surfactant, amino acids, or the like, to improve the particle formation method, particle size, or the like.

The dry powder composition may be delivered to the respiratory tract by inhalation through the mouth or through the nose, or both. In a specific embodiment, in order to provide a dry powder composition which will be effective for delivery throughout the respiratory tract for treatment or preventive treatment, the dry powder composition comprises a fine particle fraction as measured according to the Andersen Cascade Impactor (ACT) of less than about 5.8 µm of at least about 20%, and in a more specific embodiment, a fine particle fraction less than about 3.3 µm of at least about 10%. In a further embodiment, the dry powder composition comprises a fine particle fraction of less than about 5.8 µm ranging from 35 to 50%, and a fine particle fraction less than about 3.3 µm ranging from 15 to 30%.

The dry powder composition may optionally further include one or more additional active agents. In one specific embodiment, the additional active agent comprises an adjuvant, an analgesic, anti-cancer agent, antimicrobial agent, vaccine, antiviral agent, antifungal agent, antibiotic, immune suppressant, thrombolytic, anticoagulant, central nervous system stimulant, decongestant, diuretic vasodilator, antipsychotic, sedative, anesthetic, anti-inflammatory, antioxidant, or antihistamine, or a combination of two or more thereof. In a more specific embodiment, the additional active agent comprises an anti-cancer agent. In a yet more specific embodiment, the anti-cancer agent may comprise a prostanoid such as iloprost, beraprost, or treprostinil, as disclosed in the Keith et al U.S. Patent Application No. 2006/027654.6 A1, which is incorporated herein in its entirety.

In additional embodiments, an additional amount of myo-inositol is delivered to the individual in a form other than an inhalable dry powder, either prior to or following the delivery of the inhalable powder composition comprising myo-inositol example, the additional amount of myo-inositol may be delivered orally to the gastrointestinal tract of the individual, or by sublingual administration. In a specific embodiment, the additional amount of myo-inositol is delivered by sublingual administration of a wafer comprising myo-inositol. In a specific embodiment, suitable waters comprising Myo-inositol are prepared by compression of a dry powder composition comprising myo-inositol as described in further detail below.

In one embodiment, the dry powder composition comprising an effective amount of myo-inositol is provided in a tobacco product, for example in a cigarette or cigar, or in a smokeless tobacco chew product. In a specific embodiment, the dry powder composition is provided in a tobacco product, for example, a cigarette, in a location adapted for inhalation of the composition during use of the product. For example, in a cigarette, the dry powder composition is provided in a filter, a porous mesh compartment, for example, a porous mesh bag, or other area which allows inhalation of the composition during smoking of the cigarette to deliver the composition to the individual's respiratory track.

In another embodiment of the inventive methods of treating and/or delaying onset of dysplastic lesions in the bronchial airway of an individual, the methods comprise sublingually delivering a wafer comprising an effective amount of myo-inositol as detailed above to the individual. Within the present specification and claims, the term "wafer" refers to a relatively thin unit dose form suitable for sublingual application. In specific embodiments, the water has a thickness less than about 2 mm, or, more specifically, a thickness of about 1 mm. The wafer may be in the shape of a disk, square, ellipsoid, banana, or other configuration, as desired, and may have a diameter or length and width dimensions in the range of about 4-10 mm. In one embodiment, the wafer has a disk configuration with a diameter of about 6-8 mm and a thickness of about 1 mm.

In a specific embodiment, the wafer comprises a compressed dry powder of myo-inositol as described above, which, in one embodiment, may be formed according to the CAN-BD process. The wafer may include one or more excipients in addition to the dry powder composition, as desired. Excipients traditionally used by the pharmaceutical industry and Generally Regarded As Safe (GRAS) in the formation of oral tablets may be used. The excipients are typically blended with the myo-inositol based dry powder and compressed. For example, one or more binding agents and/or disintegration agents may be employed. Suitable binding agent or disintegration agents include, but are not limited to, pelleting grade sucrose, sorbitol, lactose, trehalose, mannitol, starch, guar gum, methyl cellulose, hydroxypropyl cellulose, hydroxypropyl methyl cellulose, polyvinyl pyrrolidone, polyethylene glycol, maltodextrin, and the like. Conventional additives such as mold release agents, for example magnesium stearate, muco adhesive agents, for example chitosan, flavoring agents, and the like, may also be employed. Typically, such wafers may be formed by pressing with conventional equipment at suitable pressures. For example, suitable pressures, are in the range of greater than 1 psi, or more specifically, greater than about 10 psi. In specific embodiments, the wafers may be formed by pressing with conventional equipment at pressures in a range of about 10 to less than about 100 psi, more specifically about 10 to about 80 psi, or about 10 to about 50 psi, or at pressures greater than about 100 psi, or up to about 500, about 1000 or about 2000 psi, i.e., in the range of about 500-2000 psi, or, more specifically, about 1000 psi. In cases where one or more sensitive biological materials are included in the wafer, for example, an enveloped virus vaccine, lower pressures in the range of about 1 psi to about 500 psi, more specifically, about 10 to about 100 psi, are preferable.

The wafers which are administered sublingually will desirably disintegrate in saliva to disperse the myo-inositol. In one embodiment, the wafers dissolve in wateroo temperature in less than about one minute. In another embodiment, the wafers dissolve in saliva in from about 15 to 30 seconds.

Additional wafers within the scope of the invention will be described hereafter as well.

In the methods of treating and/or delaying the onset of dysplastic lesions in the bronchial airway of an individual by sublingually delivering a wafer comprising an effective amount of myo-inositol, it is also within the scope of the present invention to include an additional step of delivering an additional amount of myo-inositol to the individual by an administration route other than sublingually. For example, in one embodiment, the additional amount of myo-inositol is delivered orally to the gastrointestinal tract of the individual.

The myo-inositol wafer employed in the methods of treating and/or delaying onset of dysplastic lesions may, if desired, further include an additional active agent. In a specific embodiment, the additional active agent comprises an adjuvant, an analgesic, anti-cancer agent, antimicrobial agent, vaccine, antiviral agent, antifungal agent, antibiotic, immune suppressant, thrombolytic, anticoagulant, central nervous system stimulant, decongestant, diuretic vasodilator, antipsychotic, sedative, anesthetic, anti-inflammatory, antioxidant, or antihistamine, or a combination of two or more thereof. In a more specific embodiment, the additional active agent comprises an anti-cancer agent, in a yet more specific embodiment, the anti-cancer agent may comprise a prostanoid such as iloprost, beraprost, or treprostinil, as disclosed in the Keith et al U.S. Patent Application No. 2006/0276546 A1.

In another embodiment, the present invention is directed to methods for administering a vaccine to an individual. In specific embodiments, the vaccines described in the present specification may be vaccines for a virus or bacteria. The methods employ combination administration which offer benefits that a single administration route or form may not. For example, the combination administration methods of the invention offer additional transport, deposition, and/or dissolution resulting in induction of an immune response in several modes. Therefore, an immune response can occur through more than one system in the body, i.e., in the respiratory tract and a gastrointestinal or injection initiated plasma system. Delivery to various locations in the body induce combined responses, i.e., both humoral and mucosal immunity. Any suitable vaccine may be administered in the methods of the invention. In a specific embodiment, the vaccine comprises a vaccine for a virus or bacteria, and in a more specific embodiment, the vaccine comprises a measles vaccine, a rubella vaccine, a tuberculosis vaccine, a human papillomavirus vaccine, an influenza vaccine, a mumps vaccine, a yellow fever vaccine, a rotavirus vaccine, a cholera vaccine, a Pseudomonas aeruginosa vaccine, an anthrax vaccine, or a combination of two or more thereof. In a more specific embodiment, the vaccine comprises a measles vaccine. In another specific embodiment, the vaccine comprises a measles vaccine and a rubella vaccine in combination. In yet another embodiment, the vaccine comprises one or more tuberculosis (TB) vaccines. Further, the vaccine may include an adjuvant if desired. Vaccine adjuvants are known in the art and may include, but are not limited to, ovalbumin, MF59 microemulsion, polylactic-glycolic acid (PLGA), CpG oligonucleotides, saponin and saponin derivatives such as QS21, alum, Freund's complete adjuvant, B30-MDP, LA-15-PH, monophosphoryl/Lipid A (MPL), and the like. Alum has been widely used as an adjuvant in injected vaccines but has not been approved for inhalation.

In a first embodiment, the methods for administering a vaccine to an individual using a combination administration comprise administering a first portion of the vaccine to the individual sublingually and administering a second portion of the vaccine to the individual by an administration route other than sublingually, wherein the first portion and the second portion combined provide an effective amount of the vaccine. The combined administration provides good immunity and may allow reduced dosages and/or improved immunity effects. The second route of administration can be oral administration to the gastrointestinal tract, inhalation, i.e., through the mouth or nose or both, or injection, for example intravenous, subcutaneous, intramuscular, or the like. In one embodiment, the second portion of the vaccine is in the form of an inhalable dry powder composition and is administered to the individual by inhalation through the mouth. In another embodiment, the second portion of the vaccine is in the form of an inhalable dry powder composition and is administered to the individual by inhalation through the nose.

In a second embodiment, the methods for administering a vaccine to an individual using a combination administration comprise administering a first portion of the vaccine to the individual via a first route comprising sublingually, orally to the gastrointestinal tract, inhalation, or injection, and administering a second portion of the vaccine to the individual by an administration route other than the first route, wherein the first portion and the second portion combined provide an effective amount of the vaccine. In a specific embodiment, the first route comprises sublingually and the second route comprises inhalation. In more specific embodiments, the first route comprises sublingually and the second route comprises inhalation, and the vaccine comprises measles vaccine or human papillomavirus vaccine. In another specific embodiment, the first route comprises inhalation and the second route comprises injection, and more specifically, the first route comprises inhalation and the second route comprises injection, and the vaccine comprises human papillomavirus vaccine. In further specific embodiments, the first route comprises sublingually and the second route comprises orally to the gastrointestinal tract. In any of the embodiments wherein one of the routes of administration is sublingually, the vaccine may be in the form of a wafer. The wafer may optionally be in the form of any of the wafers described herein, although other wafers may be employed as well. Water administration may provide the benefit of not requiring cold chain handling for distribution and administration. Additionally, administration of a wafer does not require skilled medical personnel. In any of the embodiments wherein one of the routes of administration is by inhalation, any of the dry powder compositions as described herein may be employed, although other dry powder compositions may be employed as well.

In a third embodiment, the methods for administering a vaccine to an individual using a combination administration comprise administering a vaccine in the form of an inhalable powder including both nanoparticles and microparticles that are sized for delivery to various locations in the body to induce combined responses, i.e., both humoral and mucosal immunity. More specifically, in one specific embodiment, the vaccine in the form of an inhalable dry powder composition comprises a combination of nanoparticles having a diameter less than 1 μm and microparticles having a diameter greater than 20 μm. In a more specific embodiment, the dry powder composition comprises at least about 10% particles having a diameter not greater than about 3 μm, at least about 10% particles having a diameter of about 5-10 μm, and at least about 10% particles having a diameter of at least about 20 μm, and, in a more specific embodiment, further comprises at least about 10% particles having a diameter of about 3-5 μm. Any of the aforementioned dry powder compositions may be employed, although other dry powder compositions may be employed as well. Further, any of the aforementioned vaccines may be employed, although other vaccines may be employed as well. In specific embodiments, the vaccine comprises a measles vaccine, alone or in combination with a rubella vaccine. In a further embodiment, the dry powder composition comprises myo-inositol.

In another embodiment, the present invention is directed to wafers comprising a compressed dry powder composition comprising myo-inositol. The myo-inositol may be employed as an active ingredient, for example for use in a method of treating and/or delaying onset of dysplastic lesions in the bronchial airway, wherein the myo-inositol is used in an effective amount for the indicated therapy. Alternatively, the myo-inositol may be used as a carrier for an active agent, for example, for use in therapeutic methods wherein myo-inositol is not an effective active agent. In a specific embodiment, the wafer has a thickness of not greater than about 2 mm and dissolves in water at room temperature in less than about one minute.

Whether or not the myo-inositol is employed as an active agent, the wafers as described may also include one or more additional ingredients which are active agents. Exemplary active agents include, but are not limited to, an adjuvant, an analgesic, anti-cancer agent, antimicrobial agent, vaccine, antiviral agent, antifungal agent, antibiotic, immune suppressant, thrombolytic, anticoagulant, central nervous system stimulant, decongestant, diuretic vasodilator, antipsychotic, sedative, anesthetic, anti-inflammatory, antioxidant, or antihistamine, or a combination of two or more thereof.

In a specific embodiment, the active agent comprises a vaccine. In a more specific embodiment, the vaccine comprises a vaccine for a virus or bacteria, and in a more specific embodiment, the vaccine comprises a measles vaccine, a rubella vaccine, a tuberculosis vaccine, a human papillomavirus vaccine, an influenza vaccine, a mumps vaccine, a yellow fever vaccine, a rotavirus vaccine, a cholera vaccine, a Pseudomonas aeruginosa vaccine, an anthrax vaccine, or a combination of two or more thereof. In a more specific embodiment, the active agent comprises a measles vaccine, alone or in combination with a rubella vaccine.

In another embodiment, the present invention is directed to a wafer comprising a compressed dry powder composition comprising a vaccine and a carrier, wherein the wafer has a thickness of not greater than about 2 mm and dissolves in water at room temperature in less than about 10 minutes, or, more specifically, less than about 5 minutes, less than about 2 minutes, or less than about one minute. In a specific embodiment, the vaccine comprises a vaccine for a virus or bacteria, and in a more specific embodiment, the vaccine comprises a measles vaccine, a rubella vaccine, a tuberculosis vaccine, a human papillomavirus vaccine, an influenza vaccine, a mumps vaccine, a yellow fever vaccine, a rotavirus vaccine, a cholera vaccine, a Pseudomonas aeruginosa vaccine, an anthrax vaccine, or a combination of two or more thereof. In a more specific embodiment, the vaccine comprises a measles vaccine. The wafer may comprise, for example, myo-inositol sucrose, mannitol, or trehalose. In a specific embodiment, the dry powder composition is prepared according to the CAN-BD process, and has the fine particle fractions and low moisture content as described above.

The vaccine-containing wafers promote rapid dissolution of the vaccine and restore propagation and virus or virus-like particle protein implantation in the gingiva, buccal, and tongue mucosal cells, as well as the mandibular lymph nodes. Any one or a combination of these delivery sites can be expected to induce an immune response to provide protection against the disease, for example, measles, rubella, HPV, especially the 4 main serotypes of human papillomavirus, and/or multiple influenza virus strains.

The aforementioned wafers may include one or more excipients in addition to the dry powder composition, as desired. In order to formulate a vaccine that takes the shape of a sublingual wafer, for example, when compressed using a pellet press, the dry powder which is originally designed to be free-flowing is advantageously combined with selected excipients that demonstrate adhesive behavior, but do not negatively impact the effectiveness or potency of the vaccine. Excipients traditionally used by the pharmaceutical industry and Generally Regarded As Safe (GRAS) in the formation of oral tablets may be used. The excipients are typically blended with the myo-inositol based dry powder and compressed. For example, one or more binding agents and/or disintegration agents may be employed. Suitable binding agent or disintegration agents include, but are not limited to, pelleting grade sucrose, starch, guar gum, methyl cellulose, hydroxypropyl cellulose, hydroxypropyl methyl cellulose (HPMC), hydroxyethyl starch (HES), corn starch (high amylase), polyvinyl pyrrolidone (PVP), polyethylene glycol (PEG), polyvinyl alcohol, microcrystalline cellulose (MCC), carboxymethylcellulose (CMC), sorbitol, and the like, and combinations thereof. In a specific embodiment, a combination of HPMC, PVP and MCC is employed in combination with myo-inositol. This combination has advantageously been found to provide sufficient binding to allow wafer formation at lower pressures, i.e., less than about 100 psi. This is an important feature as many vaccine viruses may be inactivated if compressed at higher pressures typically employed in wafer formation. Moreover, this combination provides wafers that advantageously disintegrate in water or saliva in less than about 1 minute. In a more specific embodiment, a wafer comprises 20% HPMC, 10% PVP, 20% MCC and 50% myo-inositol, based on the combined weight of these four ingredients. In another specific embodiment, sorbitol is employed. Conventional additives such as mold release agents, for example magnesium stearate, muco adhesive agents, for example chitosan, flavoring agents, for example menthol, and the like, may also be employed. For example, small percentages of one or more muco-adhesive materials such as chitosan to foster adhesion of the wafers on desired mucosal sublingual sites may be employed. Typically, the wafers may be formed by pressing with conventional equipment at suitable pressures, i.e., in the range of greater than 10 psi. In specific embodiments, the wafers may be formed by pressing with conventional equipment at pressures in a range of 10 to less than 100 psi, more specifically 10 to 80 psi, or 10 to 50 psi, or at pressures greater than 100 psi, or up to 500, 1000 or 2000 psi. The wafers may be opaque or transparent, depending on the particle size distribution, the composition of the original powder, and the amount of powders to which various pressures are applied.

In another embodiment, the present invention is directed to methods of providing storage stable unit dosages of a vaccine. Within the present specification and claims, the term "storage stable" refers to the ability of the vaccine to continue to exhibit potency as determined by a standard plaque assay or the 50% cell culture infective dose ($CCID_{50}$) assay wherein virus is added to cells cultured in liquid media in microtiter plate wells. Both the plaque and $CCID_{50}$ assays are described in Kisich et al, Vaccine, 29:905-912 (2011), incorporated herein by reference. A single test unit consists of the entire cell layer in a well. After the virus is added to test units, it is serially diluted down the microtiter plate, and each test unit is scored as infected or not infected and the virus titer is determined by the Spearman-Karber method for calculation of $CCID_{50}$ (see Ballew, In Clinical Virology Manual; Specter, S.; Lancz, G. J., Eds.; Elsevier: New York, 1986, p 187, and Finney, Charles Griffin & Company Ltd: London, 1964, p 524). The methods according to the invention comprise individually packaging unit dosages of a dry powder composition comprising the vaccine and myo-inositol in blister compartments formed of gas and moisture resistant material. The dry powder compositions contain less than 5 weight percent water. In many cases, the dry powder compositions contain less than 2%, less than 1%, or less than 0.5% by weight water. Beyond preserving powder aerosolization and deposition properties, stabilization via residual moisture reduction is an important factor in preserving potency by preventing microorganism growth and other degradation. The blister compartments formed of gas and moisture resistant material insure that the moisture content remains low and that the vaccine is not exposed to ultraviolet radiation, oxidants or other contaminants.

In specific embodiments of the methods, the unit dosages are stable for at least 1 year when stored at 2-8° C., or, more specifically, are stable for at least 2 years when stored at 2-8° C. In one specific embodiment, the unit dosages comprise a measles vaccine which is stable for at least 1 year when stored at 2-8° C., or, more specifically, are stable for at least 2 years when stored at 2-8° C. In additional embodiments, the gas and moisture resistant material comprises a laminate including at least one aluminum foil layer and at least one polymer film layer, for example, of a polymer having oxygen, carbon dioxide and/or moisture transmission resistance. The vaccine may be any suitable vaccine, including, but not limited to a vaccine for a virus or bacteria, and in a more specific embodiment, the vaccine comprises a measles vaccine, a rubella vaccine, a tuberculosis vaccine, a human papillomavirus vaccine, an influenza vaccine, or a Pseudomonas aeruginosa vaccine, an anthrax vaccine, or a combination of two or more thereof. In one specific embodiment, the dry powder composition is in an inhalable form, while, in another embodiment, the dry powder composition is in a compressed wafer form.

In a further embodiment, the present invention is directed to dry powder compositions comprising an antibiotic for tuberculosis, more specifically, capreomycin, kanamycin and/or isoniazid. These dry powder compositions may be employed in combined administration methods as described above. In one embodiment, the powders are formed by the CAN-BD process and, optionally, may be employed in methods of providing storage stable unit dosages by individually packaging unit dosages of the dry powder composition in blister compartments formed of gas and moisture resistant material. The dry powder compositions contain less than 5 weight percent water. In many cases, the dry powder compositions contain less than 2%, less than 1%, or less than 0.5% by weight water. In a specific embodiment, the dry powder compositions comprise myo-inositol as a carrier. The particle size requirements and doses for the TB drug dry powder composition requires microparticles targeted largely to the alveolar space, where Mtb enters in the early stages of infection and also to poorly vascularized lesions and granulomas which harbor bacilli in protective microenvironments that often elude conventional therapy. Powders according to the invention having fine particle fractions as great as about 20% less than 3.3 μm aerodynamic diameter are ideal for alveolar deposition. By depositing antibiotics in the deep lung, one may be able to reach TB lesions that lack a strong blood supply, and may also increase the targeted dose to the lung airspace and tissue while reducing systemic side effects and, potentially, the length of treatment. Using inhalable antibiotics in combination with more traditional treatments of oral administration, injection and the like, provides a two-pronged attack strategy for MDR-TB. Increasing the targeted dose in the lung airspace and targeting bacteria in protective microenvironments such as those in granulomas may prevent the development of MDR-TB by ensuring that threshold doses of antibiotics reach bacteria populations that are difficult to target by traditional methods.

Various aspects of the present invention are illustrated in the following Examples.

Example 1

The myo-inositol employed in the various methods and products described herein has been studied to evaluate its safety and immunogenicity in an inhalable dry-powder measles vaccine when administered in a single dose to Rhesus monkeys. The dry powder inhaler, PuffHaler®, as disclosed by Sievers et al, was utilized, and the animals were dosed once by inhalation delivery. The control group received a marketed measles vaccine via subcutaneous injection. Animals in the treatment group received 50 mg of dry powder measles vaccine via PuffHaler® inhalation. All vaccinated animals developed protective levels of neutralizing antibodies (>120 mIU/ml). Animals remained healthy throughout the course of the study; no effects on clinical observations, body weights, respiration rates, or breathing patterns were noted. The monkeys were subsequently sent to Johns Hopkins University where they were challenged with live measles virus; neither clinical symptoms nor viremia were observed in animals immunized by inhalation through face masks.

Example 2

In this example, inhalable dry powder compositions comprising myo-inositol were produced using the CAN-BD process as described above and as set forth in FIG. 1. The process conditions for the CAN-BD were as follows:
$CO_2$ pressure: 1500 psi
Sample concentration: 10 wt %
Sample Flow rate: 0.3 ml/min
N2 outlet drying temperature: 70° C.
N2 flow rate: 35 l/min
Secondary drying: 30 mins @70° C.

In order to improve the powder attributes for use as inhalable powder, various amino acids dispersing agents were employed. Leucine, arginine, and alanine were initially screened at 5 wt % for their effects in improving the myo-inositol powder dispersibility. Powders were analyzed for particle properties (fine particle fractions, size and moisture content) and the leucine-containing formulation was selected as the best performing powder. Additional formulations were prepared to further optimize the myo-inositol-leucine powder, by varying the leucine amount (see Table 1). The rationale was to produce an inhalable myo-inositol powder with minimum amounts of dispersing agent. Powders were characterized for their fine particle fraction (Andersen Cascade Impactor, ACI), moisture content (Karl Fischer titration) and size distribution, and results are presented in Table 1. Based on the results, myo-inositol containing 1.5 wt % leucine was selected as a final formulation. This formulation was successfully processed and repeated under smaller batch (2 g) and larger batch (10 g) processing conditions to determine reproducibility. All the powders were prepared under the same processing conditions described above, similar to those used for inhalable live measles vaccine dry powders.

TABLE 1

| Batch No. | Batch size, g | Myo-inositol | Leucine | Powder Yield | ACI <5.8 μm | <3.3 μm | Moisture Content |
|---|---|---|---|---|---|---|---|
| 1 | 2 | 95 | 5 wt % | 50% | 47% | 17% | |
| 2 | 1.6 | 99 | 1 wt % | 71.5% | 55% | 25% | 0.15% ± 0.01 |
| 3 | 1.5 | 97.5 | 2.5 wt % | 70% | | | 0.23% ± 0.01 |
| 4 | 1.5 | 99.5 | 0.5 wt % | | 10% | 5% | 0.11% ± 0.03 |
| 5 | 10.8 | 99 | 1 wt % | 74% | 51% | 20% | 0.2% ± 0.01 |
| 6 | 15 | 98.5 | 1.5 wt % | 57.5% | 52% | 15% | 0.2% |

Myo-inositol: leucine (weight ratio 98.5:1.5) dry powder was also tested for its moisture uptake and powder performance under high humidity conditions. Briefly, 10 mg powder replicates were placed in an open blister and exposed to 70% relative humidity (RH) for 15 mins. No moisture uptake was observed and the sample had exactly the same moisture content before and after exposure. The moisture content of powder before and after exposure was measured as 0.22 wt %. Also, no change was observed in the fine particle fractions of the powders as measured Andersen Cascade Impactor, before and after 70% RH exposure.

Example 3

In this example, thin wafers according to the present invention were formed. A dry powder composition prepared earlier by CAN-BD from 98.5% myo-inositol and 1.5% leucine generally in accordance with the technique described in Example 2 was used. Wafers having a thickness of about 1 min. in the form of rigid cylindrical disks, 7 millimeters in diameter, were prepared from the dry powder composition, or from Domino pelleting-grade sucrose, using a hand-held KBr pellet press from International Crystals Laboratories of Garfield, N.J., using a pressure of about 1000 psi for 1 minute. Solid rigid brittle wafers were formed. Additional wafers were prepared using a 1&2 Ton E-Z Pellet Press or a Port-A-Press. With the pressure gauge integrated into this equip en as possible to monitor applied pressure continually throughout the experiment. The wafers dissolved in less than one minute in water t room temperature. The wafers made from the 98.5% myo-inositol-1.5% leucine dry powder composition were transparent, as were wafers made from a measles virus vaccine placebo dry powder composition formed using 50 grams/L of myo-inositol in the CAN-BD process.

Figure 2:
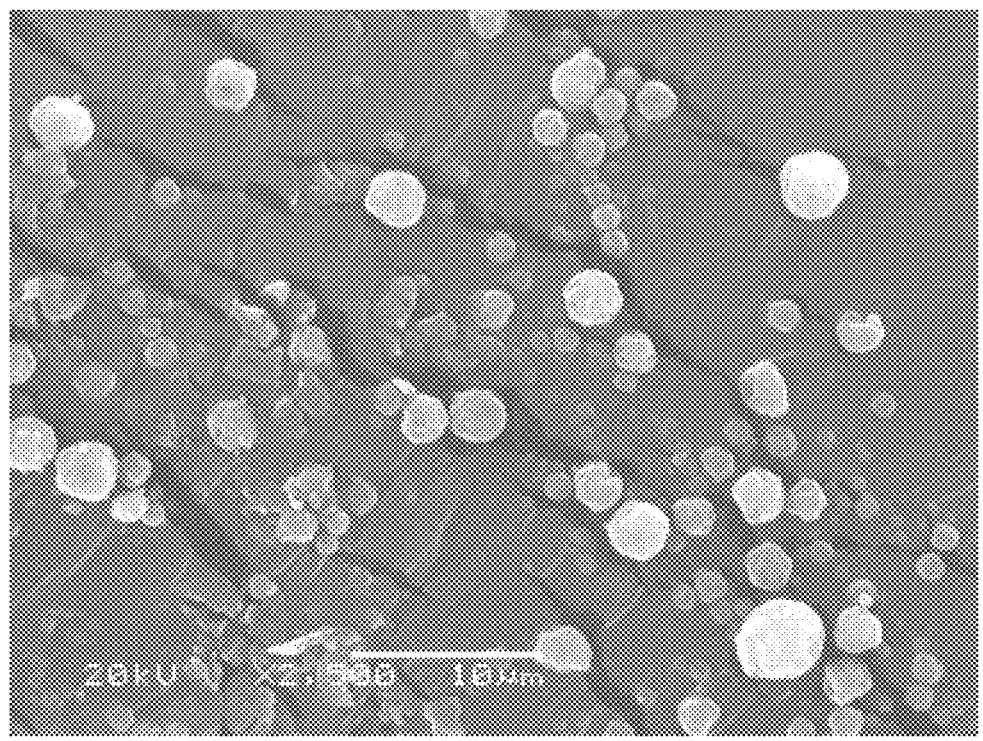
FIG. 2 is a scanning electron micrograph (SEM) showing a CAN-BD dry powder composition of 90% myo-inositol/10% leucine.
Figure 3:
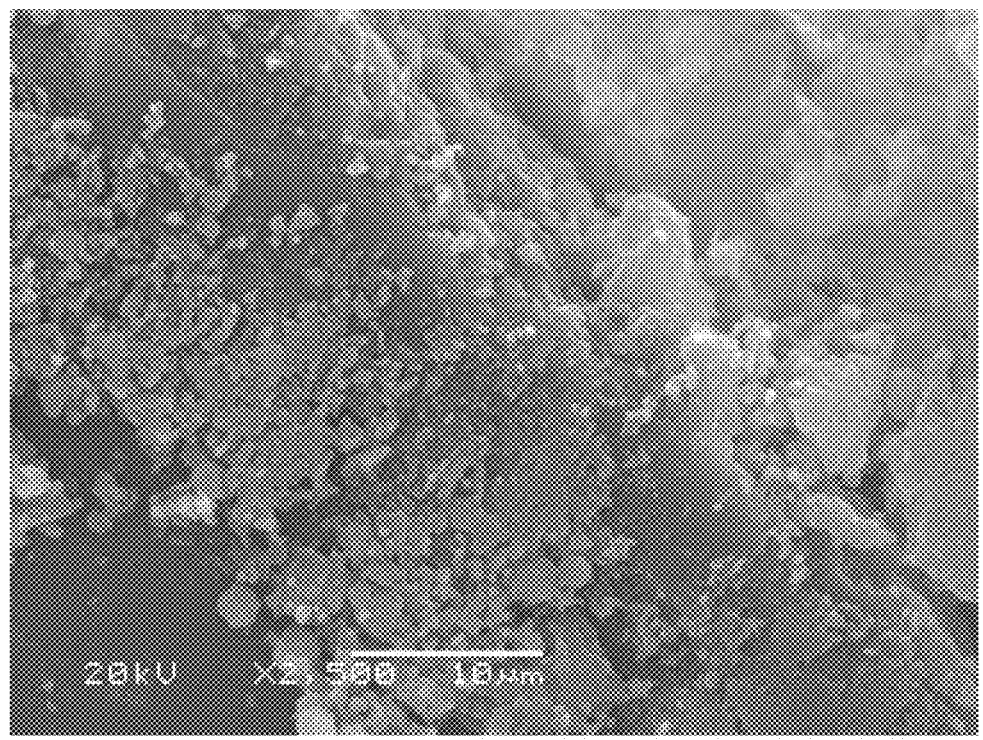
FIG. 3 is a SEM showing the surface of a highly compressed wafer disk formed from the dry powder composition by compression at 2000 psi for 15 minutes.

FIG. 2 is a scanning electron micrograph (SEM) showing of a CAN-BD dry powder composition of 90% myo-inositol/10% leucine, while FIG. 3 is a SEM showing the surface of a highly compressed wafer disk formed from the dry powder composition by compression at 2000 psi for 15 minutes. Flat glassy areas and some particles are shown at the surface.

Example 4

In this example, a measles-containing dry powder composition was prepared using the CAN-BD process as described and a measles formulation comprising Edmonston-Zagreb measles vaccine virus, myo-inositol, gelatin, arginine-HCl, histidine, alanine, lactalbumin hydrosylate, tricine buffer and additional ingredients from the Minimum Essential Medium (MEM) vaccine virus harvest fluid. Before drying, the aqueous formulations contained 11% total dissolved solids in water, and the solids comprised 50 g/L myo-inositol, 25 g/L hydrolyzed gelatin, 16 g/L arginine-HCl, 1.0 g/L alanine, 2.1 g/L histidine, 3.5 g/L lactalbumin hydrolysate, and 3.0 g/L tricine, with a pH of 6.5-7.0. The dry powder composition had a moisture content less that 3%.

Figure 4:
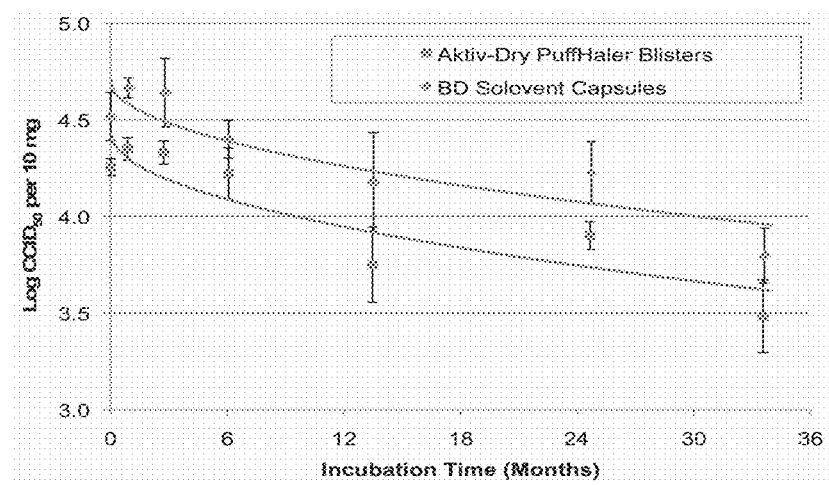
FIG. 4 shows the stability of measles vaccine virus potency for a measles vaccine dry powder formulation in blister packaging and capsule packaging over a 34 month period, as described in Example 4.

Unit dosages of the dry powder composition were stored in moisture and gas resistant blister packaging formed of aluminum foil/polymer laminate and in moisture and gas resistant capsules. The blisters and capsules were stored in foil pouches together with molecular sieve desiccant packs to maintain a very low humidity environment. The unit dosages were stored as described at 2-8° C. for almost 3 years and demonstrated excellent stability according to the $CCID_{50}$ assay. The results are set forth in FIG. 4 which shows the measles vaccine dry powder in blisters lost about 0.8 log $CCID_{50}$ of potency after 34 months and the measles vaccine dry powder in capsules lost about 0.7 log $CCID_{50}$ of potency after 34 months. These results demonstrate that the measles vaccine dry powder can be quite stable for a commercially acceptable refrigerated shelf life.

Figures 5A, 5B:
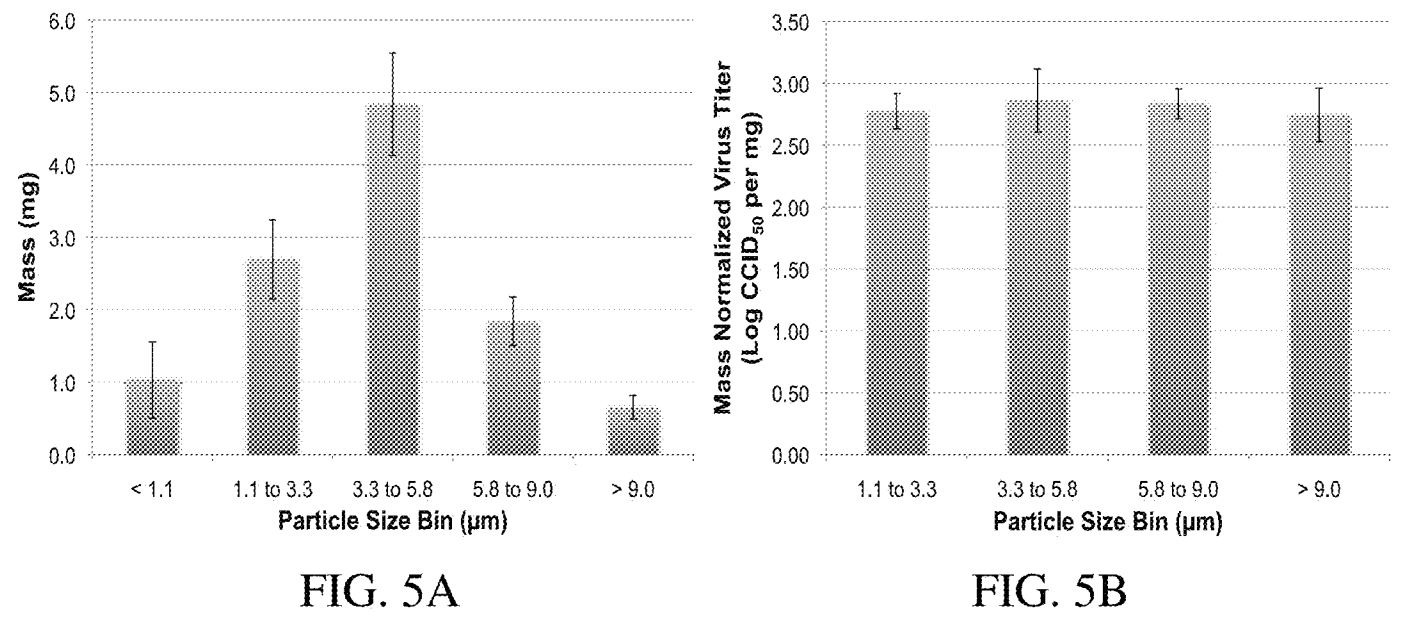

An additional experiment was conducted using samples of the blister-packaged dry powder compositions and a Puff-Haler® dry powder inhaler device from Aktiv-Dry LLC. For each experiment, 3 blister-packaged unit dosages were sequentially dispersed into a short-stack ACI configuration (Stages 0, 1, 3, 5, and F). The mass of powder that impacted on each stage was first determined gravimetrically and then the powder fractions on Stage 0 (>9.0 µm in aerodynamic diameter), Stage 1 (5.8 µm to 9.0 µm), Stage 3 (3.3 µm to 5.8 µm), and Stage 5 (1.1 µm to 3.3 µm) were recovered in a sterile manner using phosphate buffered saline (PBS). The mass of powder on the final glass fiber filter Stage F (<1.1 µm) could be weighed, but could not be reliably recovered using PBS. The vaccine virus titer in each of these samples was measured by $CCID_{50}$. As shown by the mass distribution in FIG. 5A, most of the measles vaccine dry powder particles collected on the ACI stages were in the respirable size range, i.e., <5.8 µm. Of the average 31 mg total of measles vaccine dry powder in the three PuffHaler® blisters used in each experiment, 28%±4% (s.d.) was recovered in the mass fraction <5.8 µm, and 12%±3% in the fraction <3.3 µm. In this case, a single 10 mg measles vaccine dose contained an average of 3.3 log $CCID_{50}$, of vaccine virus titer in the respirable fraction (<5.8 µm). Furthermore, the vaccine titer was uniformly distributed in the fine and course microparticles. The mass normalized titer did not change within experimental error as a function of the particle size bins as shown in FIG. 5B. These findings are very important, as they confirm the potency per unit mass of particles sized throughout the respirable range.

Example 5

A HPV-containing dry powder composition was also prepared using the CAN-BD process as described and the myo-inositol/leucine (98.5/1.5 wt ratio) and HPV16L1 capsid-based vaccine. The dry powder composition exhibited a fine particle mass fraction of 50%<5.8 µm (ACI). Unit dosages of the dry powder composition were stored in moisture and gas resistant blister packaging formed of aluminum foil/polymer laminate. SDS-PAGE analysis of the composition after processing and after the unit dosages were stored at 2-8° C. for 1 year showed no detectable degradation of HPV capsid protein.

Example 6

This example demonstrates the preparation of solid microspheres using the CAN-BD system and a water/oil/water emulsions system.

Figure 6:
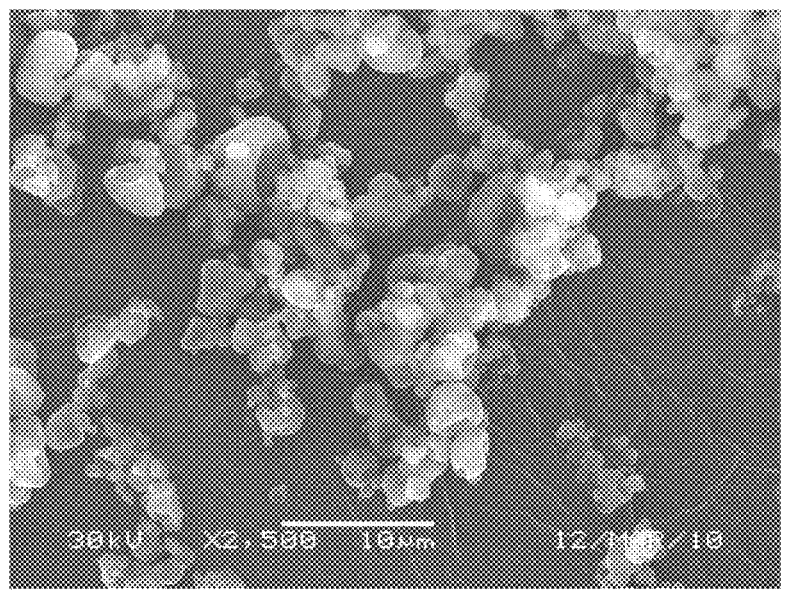
FIG. 6 is a scanning electron micrograph (SEM) showing a CAN-BD dry powder composition as described in Example 6, prepared according to the first protocol.

A first protocol, adapted from Lamprecht et al, *International Journal of Pharmaceutics*, 184(1):97-105 (1999), employed an inner water phase consisting of 500 mg of isoniazid in 10 mL of phosphate buffered saline (PBS) or distilled water. The 500 mg of isoniazid is 0.24% by mass of the entire w/o/w emulsion (210 mL including all three phases) The organic phase consists of 500 mg of PLGA (50:50) dissolved in 40 mL of ethyl acetate (EA). The first, internal water-in-oil (w/o) emulsion is created by homogenizing the isoniazid water phase and the EA organic or "oily" phase at 5000 RPM for 3 minutes. The external water phase contains 2% polyvinyl alcohol (PVA) w/v, with respect to the external water phase of 200 mL. To create the w/o/w emulsion, the 10 mL of the previously described w/o emulsion is poured into the external aqueous PVA phase and is homogenized on ice at 8000 RPM for 3 min. After homogenization the w/o/w volume expands from 210 mL to 450 mL with two phases—a foam phase and a liquid phase. The foam phase has been evaluated by SEM and does not contain any significant concentration of particles. The liquid phase is poured into the product solution cylinder of the CAN-BD system where the emulsion was dried via at 60° C., 30 L/min $N_7$, 1260 psi, with a flow rate of 0.5 mL/min. This procedure was used to prepare microspheres from emulsions containing about 0.2-0.8 isoniazid, about 0.2-0.8 and about 1-2% PVA. The resulting particles are spherical with dimples and range in size from about 0.25 µm to about 7 µm. Microspheres produced using an emulsion containing 0.19% isoniazid, 0.24% PLGA and 1.92% PVA with PBS, EA and water are shown in FIG. 6.

Figure 7:
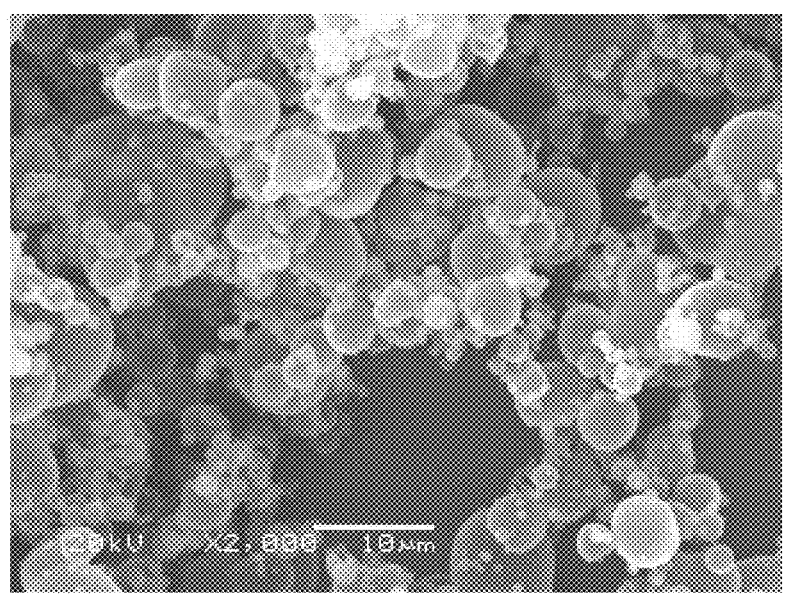
FIG. 7 is a scanning electron micrograph (SEM) showing a CAN-BD dry powder composition as described in Example 6, prepared according to the second protocol.

In a second protocol, adapted from Song et al, *Colloids and Surfaces A: Physicochem. Eng. Aspects*, 276:162-167 (2006), 100 mg of PLGA (75:25) is dissolved in 10 mL of EA. The organic phase is added to 20 mL of an aqueous phase containing the stabilizer PVA. The PVA aqueous phase is 1% w/v with respect to the 20 mL water phase. The mixture is allowed to come to saturation and is then emulsified for one minute with a probe tip sonicator operating at setting six and between 1-10% intensity. While sonicating, the external aqueous phase which consists of 80 mL of water and dissolved drug is added to the w/o emulsion created by the sonication of the PLGA/EA phase and the water PVA phase. After sonication 30 mL of the w/o/w emulsion is processed via the CAN-BD system at 0.5 mL/min, 30 L/min $N_2$, 60° C. and between 1200 and 1260 psi. The particles made using protocol 3 employed bovine serum albumin (BSA) as a model protein are shown in FIG. 7. These particles are generally range in size from about 0.25 µm to about 7 µm.

The various examples and embodiments described herein are illustrative in nature only and are non-limiting of the invention defined by the claims. Additional embodiments of the invention within the scope of the claims will be apparent to one of ordinary skill in the art in view of the present disclosure.

What is claimed is:

1. A tobacco product, including a dry powder composition comprising an amount of myo-inositol effective for treating dysplastic lesions in the bronchial airway of an individual, wherein the tobacco product is in the form of a cigarette, cigar or smokeless tobacco chew product.

2. The tobacco product of claim 1, in the form of a cigarette.

3. The tobacco product of claim 2, wherein the dry powder composition is provided in a location adapted for inhalation upon smoking of the cigarette.

4. The tobacco product of claim 2, wherein the dry powder composition is provided in a filter in the cigarette.

5. The tobacco product of claim 2, wherein the dry powder composition is provided in a porous mesh compartment.

6. The tobacco product of claim 1, in the form of a cigar.

7. The tobacco product of claim 1, in the form of a smokeless tobacco chew product.

8. The tobacco product of claim 1, wherein the dry powder composition further includes an additional agent selected from an analgesic, an anti-cancer agent, anti-inflammatory, antioxidant, or antihistamine.

9. The tobacco product of claim 1, wherein the dry powder composition further includes an anti-cancer agent.

10. A tobacco product, comprising tobacco and including a dry powder composition comprising myo-inositol, the tobacco product comprising from about 0.01 to about 10 grams of myo-inositol, wherein the tobacco product is in the form of a cigarette, cigar or smokeless tobacco chew product.

11. The tobacco product of claim 10, wherein the tobacco product comprises about 0.01 to about 5 grams of myo-inositol.

12. The tobacco product of claim 10, wherein the tobacco product comprises from about 0.5 to about 5 grams of myo-inositol.

13. The tobacco product of claim 10, wherein the tobacco product comprises from about 1 to about 5 grams of myo-inositol.

\* \* \* \* \*